US006238332B1

(12) United States Patent
Kanesaka

(10) Patent No.: US 6,238,332 B1
(45) Date of Patent: May 29, 2001

(54) RADIATION DEVICE WITH SHIELD PORTION

(75) Inventor: Nozomu Kanesaka, Old Tappan, NJ (US)

(73) Assignee: Uni-Cath Inc., Fair Lawn, NJ (US)

( * ) Notice: Subject to any disclaimer, the term of this patent is extended or adjusted under 35 U.S.C. 154(b) by 0 days.

(21) Appl. No.: 09/437,402

(22) Filed: Nov. 10, 1999

Related U.S. Application Data

(63) Continuation-in-part of application No. 09/073,813, filed on May 7, 1998.

(51) Int. Cl.$^7$ ............................................. A61N 5/00
(52) U.S. Cl. ............................................................ 600/3
(58) Field of Search ................................. 600/3, 2, 1, 4, 600/5, 6, 7, 8; 604/103.04

(56) References Cited

U.S. PATENT DOCUMENTS 5,213,561 * 5/1993 Weinstein et al. ........................ 600/7
5,383,853 * 1/1995 Jung et al. ....................... 604/103.04
5,938,582 * 8/1999 Ciamacco, Jr. et al. .................. 600/3

* cited by examiner

Primary Examiner—Eric F. Winakur
Assistant Examiner—Brian Szmal
(74) Attorney, Agent, or Firm—Kanesaka & Takeuchi

(57) ABSTRACT

A radiation device is used in a body lumen for treatment. The radiation device is formed of a sheath to be disposed in the body lumen, and an elongated radiation member. The sheath includes a guide wire passageway to allow a guide wire to pass therethrough, and a sheath passageway extending throughout a substantial portion thereof. The radiation member includes an outer member having a shield portion at a front part thereof, and an inner member slidably situated in the outer member and having a radiation portion at a front part thereof. When the radiation device is used, the sheath is introduced into a body lumen by sliding over the guide wire preliminary placed in the body lumen. Then, the radiation member is inserted into the sheath passageway in a condition such that the radiation portion is located inside the shielding portion. When radiation is required, the radiation portion is disposed outside the shield portion. Since the sheath prevents the radiation member from contacting the body lumen, the radiation member may be reused.

8 Claims, 2 Drawing Sheets

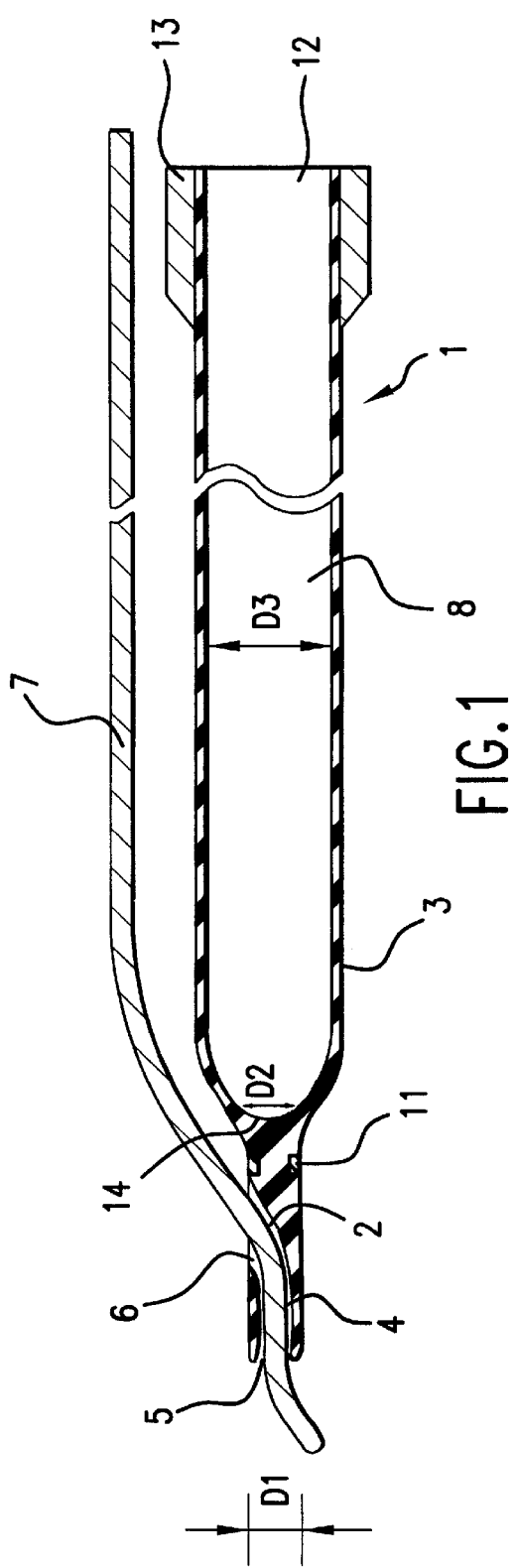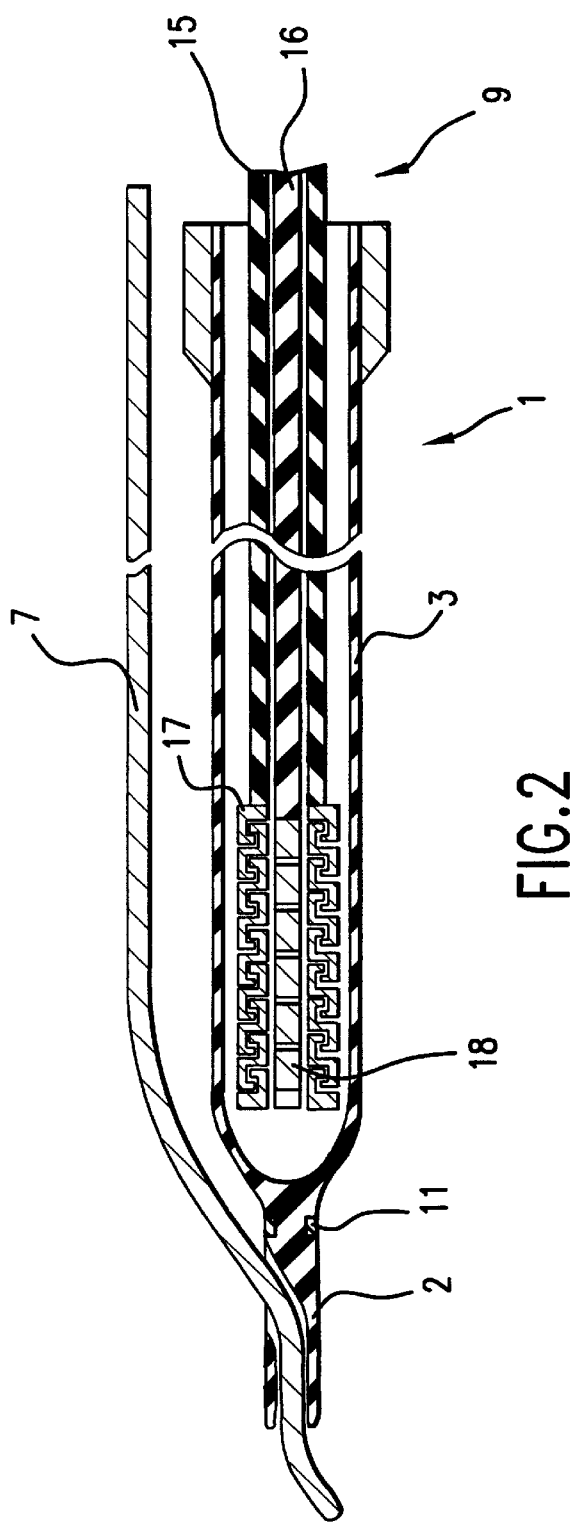

RADIATION DEVICE WITH SHIELD PORTION

CROSS REFERENCE TO RELATED APPLICATION

This is a CIP application of Ser. No. 09/073,813 filed on May 7, 1998.

BACKGROUND OF THE INVENTION AND RELATED ART STATEMENT

The invention relates to a radiation device for radiation therapy, and more particularly, a rapid exchange radiation device which is used in a percutaneous transluminal coronary angioplasty (PTCA) procedure and/or in a stent implantation into a patient's body lumen.

The PTCA procedure has been a standard procedure for re-vascularization of coronary artery. For example, in the PTCA procedure, a catheter having a balloon at the distal end is introduced into the coronary artery to enlarge a stenosis, i.e. constriction in the coronary artery. However, re-stenosis and re-closure of the lesion after the PTCA procedure is a problem thereafter. Namely, in 35 to 40 percent of the angioplasty cases, re-stenosis occurs within 6 months after the PTCA procedure.

In the treatment of the stenosis in the artery, there has been used another device called "stent", i.e. generally tubular shaped device which functions to support a desired part of the artery, such as a lesion enlarged by a balloon catheter, from the inside thereof. The stent prevents occurrence of re-stenosis, and lowers the rate of re-stenosis to 13 to 19%. Furthermore, according to the recent study, radiation therapy combined with a stent implantation has shown better results, and lowers the rate of occurrence of re-stenosis to 1 to 9%. Therefore, it is better to use radiation therapy combined with the stent implantation in the PTCA procedure for preventing re-stenosis.

Radiation therapy as stated above can be used in the standard PTCA procedure alone as well as in the PTCA procedure combined with the stent implantation. In either case, the lesion is exposed to the pre-calculated dosage of radiation. It is believed that the exposure to radiation would partially destroy DNA of target cells damaged by the PTCA procedure or stent procedure, so that the excessive proliferation of the cells damaged by the PTCA procedure or stent procedure can be minimized.

There are several methods of applying radiation to the target cells or lesion. In the first method, a guide wire generally used in the PTCA procedure is provided with a radioactive core imbedded at the tip thereof, and radiation is applied by the radioactive core in the guide wire. In the second method, radioactive pellets or cells are mechanically located to the lesion site, and radiation is applied by the radioactive pellets or cells. After desired exposure of radiation to the lesion, the radioactive pellets or cells are removed from the lesion by the mechanical system. In the third method, radioactive fluid is injected into a PTCA balloon catheter which is frequently used in the PTCA procedure, so as to apply radiation to the target lesion.

In the above described methods, however, there are following disadvantages. Firstly, since the radioactive pellets or the device having the radioactive source, such as the guide wire having the radioactive source at the tip thereof, are placed directly inside a patient's body lumen, such as an artery, the radioactive pellets or the device with the radioactive source are not used again.

Also, in the method using the guide wire with the radioactive source at the tip thereof, in order to apply radiation therapy, the guide wire preliminary inserted inside the patient's lumen for another treatment in the PTCA procedure has to be withdrawn first, and the guide wire having the radioactive core has to be introduced inside the patient's body lumen again to locate the tip of the guide wire at the lesion. Thus, exchange of the guide wire in the meandering body lumen is cumbersome and may cause damage to the artery or blood vessel.

Furthermore, after enough dosage of radiation is applied to the lesion, the radiation catheter is required to be withdrawn as quickly as possible so as not to cause excessive radiation. Also, it is required that the radiation device should be handled quickly because of its affect to other people. Thus, it has been sought that the radiation therapy can be made easily and quickly.

Accordingly, an object of the invention is to provide a radiation device, which can provide radiation only to a required portion in a body lumen at a required time.

Another object of the invention is to provide a radiation device as stated above, wherein a radiation source can be placed inside the body lumen smoothly and rapidly, and can be removed quickly from the required portion after enough dosage of radiation.

A further object of the invention is to provide a radiation device as stated above, wherein the radiation source once used inside the patient's body lumen can be reused.

A still further object of the invention is to provide a radiation device as stated above, wherein the radiation source can be introduced into the required portion by a guide wire used in the general PTCA procedure.

Further objects and advantages of the invention will be apparent from the following description of the invention.

SUMMARY OF THE INVENTION

A radiation device of the invention is designed to be disposed in a body lumen. The radiation device is formed of a sheath to be disposed in the body lumen, and an elongated radiation member. The sheath includes a guide wire passageway to allow a guide wire to pass therethrough, and a sheath passageway extending throughout a substantial portion thereof. The elongated radiation member is inserted into the sheath passageway.

The radiation member includes an outer member having a shield portion at a front part thereof, and an inner member slidably situated in the outer member and having a radiation portion at a front part thereof. The inner member is arranged in the outer member such that when radiation is not required, the radiation portion is located inside the shield portion, and when radiation is required, the radiation portion is disposed outside the shield portion. Since the radiation member is inserted into the sheath passageway, the radiation member is not contaminated at all by the use. It is possible to use the radiation member to different patients.

When the radiation device of the invention is used, firstly, the guide wire is introduced inside the body lumen to be located at the lesion, and the sheath is introduced into the lesion by sliding along the guide wire. Then, the radiation member including the inner and outer members is slid into the sheath passageway. At this time, the radiation portion of the inner member is located inside the shield portion of the outer member.

When the radiation therapy is made, the radiation portion is disposed outside the shield portion by moving the inner or outer member to thereby apply radiation to the lesion. After the adequate exposure of radiation to the lesion, the inner or outer member is moved to locate the radiation portion inside the shield portion, and then, the radiation member including the inner and outer members is quickly and easily withdrawn from the sheath. Therefore, the radiation member can be reused for another patient or another procedure, and overdosing of radiation can be prevented.

BRIEF DESCRIPTION OF THE DRAWINGS

FIG. 1 shows a cross sectional view of a radiation device with a guide wire, wherein an elongated radiation member is removed according to the present invention;

FIG. 2 shows a cross sectional view of the radiation device, in which the elongated radiation member in a state that a radiation portion is located inside a shield portion is inserted;

DETAILED DESCRIPTION OF PREFERRED EMBODIMENTS

Figure 3:
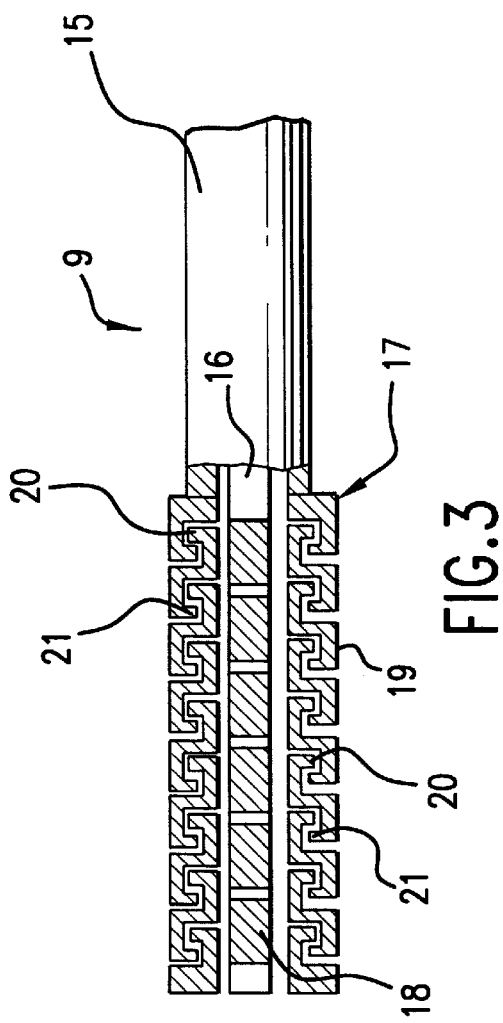
FIG. 3 shows an enlarged cross sectional view of the elongated radiation member in the state that the radiation portion is located inside the shield portion.

With reference to the attached drawings, embodiments of the invention will be explained hereinafter.

As shown in FIGS. 1 and 2, a radiation device 1 is a rapid exchange type, and is formed of a front part or guide wire receiving part 2, a sheath 3 extending rearwardly from the front part 2, and an elongated radiation member 9 to be disposed in the sheath 3. In the guide wire receiving part 2, there is formed a guide wire passageway 4 for receiving a guide wire 7 therein. The guide wire passageway 4 extends from a front port 5 formed at a tip of the guide wire receiving part 2 to a side port 6 formed in a side wall of the guide wire receiving part 2.

As shown in the figures, the side port 6 is relatively larger than the front port 5 for facilitating smooth movement of the guide wire 7 in the guide wire passageway 4. The guide wire receiving part 2 has a diameter D1 smaller than a diameter D3 of the middle part of the sheath 3, so as to facilitate introduction of the radiation device 1 in the narrow and meandering body lumen, such as an artery.

The sheath 3 has a catheter passageway 8 therein, which is an elongated hole extending in the substantially entire length of the sheath 3 from a proximal open end 12 with a flange 13 to an end 14 closed and located adjacent to the guide wire receiving part 2. As shown in the figures, a distal end part of the catheter passageway 8 is gradually tapered toward the end 14 to be inserted into the narrow body cavity. As shown in FIG. 1, a diameter D2 at the end 14 is smaller than the diameter D3 at the middle part of the sheath 3.

The elongated radiation member 9 to be inserted into the sheath 3 is formed of an outer member 15 and an inner member 16 slidably situated inside the outer member 15. The outer member 15 has a shield portion 17 at a front portion thereof, while the inner member 16 has a radiation portion 18 at a front portion. The radiation portion 18 includes a radiation material, such as radiation pellets, known already in the art, and includes holes 18' to provide flexibility of the radiation portion.

Figure 4:
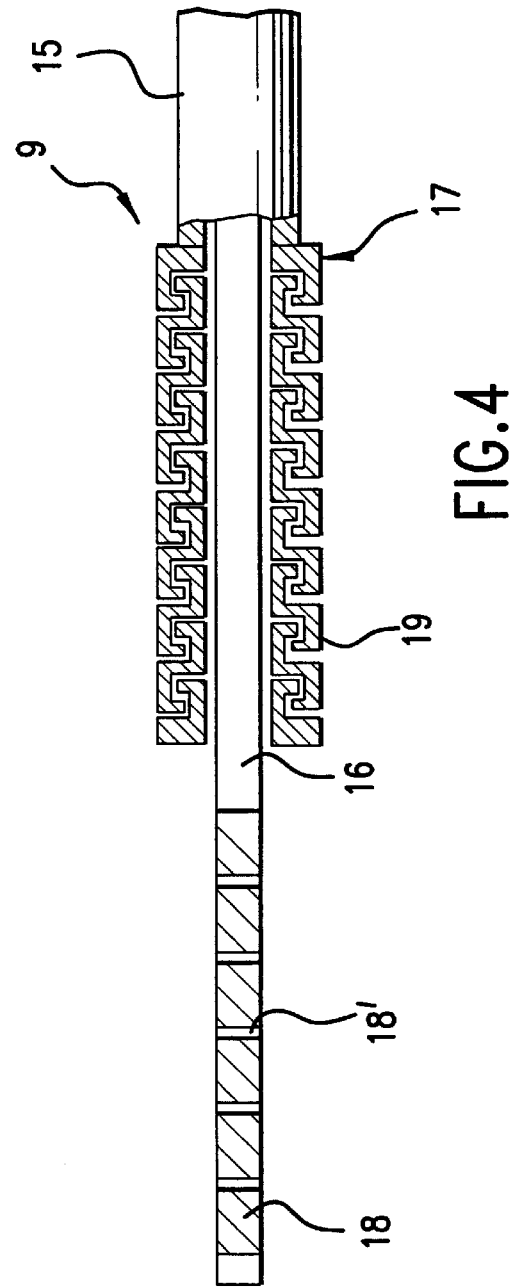
FIG. 4 shows an enlarged cross sectional view of the elongated radiation member in a state that the radiation portion is located outside the shield portion.

As clearly shown in FIGS. 3 and 4, the shield portion 17 is formed of a plurality of annular members 19 to shield radiation of the radiation portion 18. The annular member 19 includes an inner engaging portion 20 and an outer engaging portion 21. An inner engaging portion 20 in one annular member engages an outer engaging portion 21 in the adjacent annular member to extend laterally. Since a space is formed between the adjacent annular members 19, the shield portion 17 formed of the annular members 19 can be bent in the longitudinal direction along the sheath 3.

The annular member 19 may be made of a lead plate with a thickness of 0.7 mm to sufficiently shield radiation of the radiation portion 18. On the other hand, the shield portion 17 may be made of resin containing shield particles, such as lead particles, therein. In this case, the shield portion 17 may be formed integrally with the outer member 15. Similarly, the radiation portion 18 may be formed of resin with radiation particles and formed integrally the inner member 16.

As shown in FIG. 3, when the radiation member 9 is inserted into the sheath 3, the radiation portion 18 is substantially enclosed or covered by the shield portion 17. When the radiation therapy is conducted, the outer member 15 is pulled to expose the radiation portion outwardly. When the radiation therapy is finished, the outer member 15 is pushed to cover the radiation portion 18. Thus, only when the radiation therapy is conducted, the radiation portion 18 is exposed to a required area. Other areas are not exposed to radiation even when the radiation member 9 is inserted into the sheath 3.

In the radiation therapy during a PTCA procedure, the guide wire 7 is preliminary inserted into a patient's body lumen, such as a coronary artery, to be located at a lesion which requires a treatment. Incidentally, the guide wire which has been already introduced for another treatment in the PTCA procedure can be used as the guide wire 7. Then, the sheath 3 is inserted over the guide wire 7 to be located at the lesion in the artery. Namely, a proximal end of the guide wire 7, not shown, is inserted into the front port 5 to pass through the guide wire passageway 4. Then, by sliding the sheath 3 along the guide wire 7, the sheath 3 is guided and placed at the lesion in the artery. Since the guide wire passageway 4 of the sheath 3 is relatively short, the sheath 3 can be easily transferred over the guide wire 7. Namely, in case of emergency, the sheath 3 can be removed from the artery by sliding over the guide wire 7 or exchanged quickly.

As shown in FIG. 2, after the sheath 3 is placed at the lesion in the artery through the guide wire 7, the radiation member 9 in a condition that the radiation portion 18 is located inside the shield portion 17 as shown in FIG. 3 is inserted into the catheter passageway 8 of the sheath 3 such that the distal end of the radiation member 9 is located at the end 14 of the catheter passageway 8. When radiation is to be applied to the lesion, the outer member 15 is pulled such that the radiation portion 18 is exposed outside the shield portion 17, and the radiation portion 18 is left as it is until the desired dosage of radiation is applied to the lesion.

When the desired dosage of radiation is applied, the outer member 15 is pushed to cover the radiation portion 18 by the shield portion 17. Thus, radiation to the lesion by the radiation potion 18 is terminated. In this condition, the radiation member 9 is quickly pulled out from the sheath 3 to the outside of the patient's artery. Then, the sheath 3 is withdrawn over the guide wire 7 from the artery, or may be left in the artery if any further therapy regarding PTCA procedure is required.

Preferably, in the front part 2 near the sheath 3, a marker 11 is provided. During the radiation therapy, the radiation portion 18 provided at the distal end of the inner member 16 should be located at the end 14. Since the marker 11 can identify the location of the end 14, it is confirmed by the marker 11 that the radiation portion 18 can be adequately located at the lesion for radiation therapy.

As described above, the radiation member to be inserted into the sheath is formed of the inner and outer members having the shield portion and radiation portion, and only when radiation is conducted, the outer member is moved. Thus, radiation is applied only to a required portion at a required time.

Also, in the present invention, by providing the sheath outside the radiation member, the radiation member is insulated from the body lumen, i.e. blood, throughout the radiation therapy including introduction into and withdrawal from the artery. Therefore, the radiation member with the radiation portion can be reused for other treatments. Thus, the cost of the radiation therapy can be lowered.

Further, in the present invention, after the desired exposure of radiation, the radiation member with the radiation portion can be easily withdrawn from the sheath. Thus, the exchange and/or withdrawal of the radiation member can be quickly operated.

While the invention has been explained with reference to the specific embodiments of the invention, the explanation is illustrative and the invention is limited only by the appended claims.

What is claimed is:

1. A radiation device for a body lumen, comprising:

a sheath to be disposed in the body lumen and having a guide wire passageway adapted to allow a guide wire to pass therethrough at a front part thereof and a sheath passageway extending throughout a substantial portion thereof, said sheath passageway being completely closed except a rear end of the sheath to prevent an outer material from entering into the sheath passageway except the rear end, and an elongated radiation member to be inserted into the sheath passageway, said radiation member including an outer member having a shield portion at a front part thereof formed of a plurality of radiation shielding annular members partly overlapping with respect to each other to have flexibility thereat, and an inner member slidably situated in the outer member and having a flexible radiation portion at a front part thereof, said inner member being arranged in the outer member such that when radiation is not required, the radiation portion is located inside the shield portion, and when radiation is required, the radiation portion is disposed outside the shield portion.

2. A radiation device according to claim 1, wherein said guide wire passageway extends from a distal end of the front part to a side wall thereof so that the sheath is rapidly exchangeable with respect to the guide wire.

3. A radiation device according to claim 1, wherein said front part includes a marker at a bottom thereof.

4. A radiation device according to claim 1, wherein each annular member includes an inner engaging portion, and an outer engaging portion spaced apart from the inner engaging portion in an axial direction, one inner engaging portion in one annular member engaging one outer engaging portion in an adjacent annular member to have a space therebetween in a radial direction to thereby provide flexibility between two of the annular members.

5. A radiation device according to claim 4, wherein said flexible radiation portion includes a plurality of holes therein to provide flexibility thereat.

6. A radiation device for a body lumen, consisting of:

a sheath to be disposed in the body lumen and consisting essentially of a guide wire passageway adapted to allow a guide wire to pass therethrough at a front part thereof and one sheath passageway extending throughout a substantial portion thereof, said sheath passageway being completely closed except a rear end of the sheath to prevent an outer material from entering into the sheath passageway except the rear end, and an elongated radiation member to be inserted into the sheath passageway, said radiation member consisting essentially of an outer member having a flexible shield portion at a front part thereof, and an inner member slidably situated in the outer member and having a flexible radiation portion at a front part thereof, said inner member being arranged in the outer member such that when radiation is not required, the radiation portion is located inside the shield portion, and when radiation is required, the radiation portion is disposed outside the shield portion.

7. A radiation device according to claim 6, wherein said shield portion is formed of a radiation shielding annular members partly overlapping with respect to each other to have flexibility thereat.

8. A radiation device according to claim 7, wherein each annular member includes an inner engaging portion, and an outer engaging portion spaced apart from the inner engaging portion in an axial direction, one inner engaging portion in one annular member engaging one outer engaging portion in an adjacent annular member to have a space therebetween in a radial direction to thereby provide flexibility between two of the annular members, said flexible radiation portion having a plurality of holes therein to provide flexibility thereat.

* * * * *